US012796913B2

(12) United States Patent
Yokoi et al.

(10) Patent No.: US 12,796,913 B2
(45) Date of Patent: Nov. 17, 2026

(54) METHOD RELATED TO DRY-EYE CLASSIFICATION AND OPHTHALMOLOGIC DEVICE AND LEARNING DEVICE EMPLOYING SAME

(71) Applicants: KYOTO PREFECTURAL PUBLIC UNIVERSITY CORPORATION, Kyoto (JP); Rexxam Co., Ltd., Osaka (JP)

(72) Inventors: Norihiko Yokoi, Kyoto (JP); Jun Kawai, Kagawa (JP); Reiji Yoshioka, Kagawa (JP); Ken-ichi Yoshida, Kagawa (JP); Daichi Yamamoto, Kagawa (JP)

(73) Assignees: KYOTO PREFECTURAL PUBLIC UNIVERSITY CORPORATION, Kyoto (JP); Rexxam Co., Ltd., Osaka (JP)

( * ) Notice: Subject to any disclaimer, the term of this patent is extended or adjusted under 35 U.S.C. 154(b) by 441 days.

(21) Appl. No.: 18/553,933

(22) PCT Filed: Mar. 31, 2022

(86) PCT No.: PCT/JP2022/016580
§ 371 (c)(1),
(2) Date: Oct. 4, 2023

(87) PCT Pub. No.: WO2022/215648
PCT Pub. Date: Oct. 13, 2022

(65) Prior Publication Data
US 2024/0215820 A1 Jul. 4, 2024

(30) Foreign Application Priority Data
Apr. 5, 2021 (JP) ................................ 2021-064437

(51) Int. Cl.
*A61B 3/10* (2006.01)
*A61B 3/14* (2006.01)
(Continued)

(52) U.S. Cl.
CPC ................ *A61B 3/101* (2013.01); *A61B 3/14* (2013.01); *A61B 5/4842* (2013.01); *G06V 10/764* (2022.01); *G16H 30/40* (2018.01)

(58) Field of Classification Search
CPC ......... A61B 3/0025; A61B 3/10; A61B 3/101; A61B 3/107; A61B 3/14; A61B 5/4842; A61B 5/7264; G16H 30/40; G06V 10/764
See application file for complete search history.

(56) References Cited

U.S. PATENT DOCUMENTS

2021/0212561 A1 7/2021 Arita et al.

FOREIGN PATENT DOCUMENTS

JP 2011156030 A 8/2011
JP 2018047083 A 3/2018
(Continued)

OTHER PUBLICATIONS

Yokoi et al., "The Pardign Shift of Dry Eye in the Clinical Setting; Tear Film Oriented Diagnosis and Therapy", 2013, pp. 549-558.
(Continued)

*Primary Examiner* — Jack Dinh
(74) *Attorney, Agent, or Firm* — Troutman Pepper Locke LLP

(57) ABSTRACT

Classifying dry eye syndrome using a measurement comprising a light-projecting unit projecting a predetermined pattern onto a cornea surface, an image capturing unit that repeatedly captures a reflected images of the pattern reflected off the cornea surface, an acquiring unit that acquires blurriness information according to a value indicating a blurriness level at a maximum portion of luminance
(Continued)

values in a reflected image, for each of the captured multiple reflected images, and a classifying unit that acquires a classification result of a dry eye syndrome by applying multiple pieces of time-series blurriness information acquired by the acquiring unit to a learning model trained using multiple pairs of training input information. Providing a classification result of a dry eye syndrome corresponding to the training input information, and an output unit that outputs the classification result acquired by the classifying unit.

4 Claims, 8 Drawing Sheets

(51) Int. Cl.

| | |
|---|---|
| ***A61B 5/00*** | (2006.01) |
| ***G06V 10/764*** | (2022.01) |
| ***G16H 30/40*** | (2018.01) |

(56) References Cited

FOREIGN PATENT DOCUMENTS

| | | | |
|---|---|---|---|
| JP | 202018475 | A | 2/2020 |
| JP | 2020195883 | A | 12/2020 |
| WO | 2019168142 | A1 | 9/2019 |

OTHER PUBLICATIONS

Asatani et al., "Proposal of 3D-Conv-RNN for Movie Recognition", IPSJ SIG Technical Report, vol. 2016-CVIM-201 No. 6, dated Mar. 3, 2016.
Notice of Reasons for Refusal dated Feb. 1, 2022, from corresponding Japanese Application No. 2021-064437.
Decision of Refusal dated May 17, 2022, from corresponding Japanese Application No. 2021-064437.
International Search Report dated Jun. 21, 2022, from Corresponding International Application No. PCT/JP2022/016580.
Reconsideration Report by Examiner before Appeal dated Oct. 19, 2022, from corresponding Japanese Application No. 2021-064437.
Notice of Reasons for Refusal dated Feb. 28, 2023, from corresponding Japanese Application No. 2021-064437.

| Layer | Input Size | Output Size | Number of Filter | Size | Stride |
|---|---|---|---|---|---|
| Input layer | (100,150,150,1) | (100,150,150,1) | - | - | - |
| Convolutional layer 1 | (100,150,150,1) | (100,75,75,16) | 16 | (1,3,3) | (1,2,2) |
| Pooling layer 1 (MaxPool) | (100,75,75,16) | (100,75,75,16) | - | (1,3,3) | (1,1,1) |
| Convolutional layer 2 | (100,75,75,16) | (100,38,38,32) | 32 | (1,3,3) | (1,2,2) |
| Pooling layer 2 (MaxPool) | (100,38,38,32) | (100,38,38,32) | - | (1,3,3) | (1,1,1) |
| Convolutional layer 3 | (100,38,38,32) | (100,19,19,64) | 64 | (1,3,3) | (1,2,2) |
| Pooling layer 3 (MaxPool) | (100,19,19,64) | (100,19,19,64) | - | (1,3,3) | (1,1,1) |
| Pooling layer 4 (GlobalMaxPool) | (100,19,19,64) | (64) | - | - | - |
| Output layer (SoftMax) | (64) | (4) | - | - | - |

FIG.7

| | | Prediction | | | | |
|---|---|---|---|---|---|---|
| | | ADDE | DWDE | IEDE | DWDE+IEDE | Accuracy Rate |
| Accurate | ADDE Aqueous-deficient dry eye | **18** | 0 | 1 | 0 | 95% |
| | DWDE Decreased wettability dry eye | 5 | **19** | 0 | 1 | 76% |
| | IEDE Increased evaporation dry eye | 0 | 2 | **8** | 0 | 80% |
| | IEDE Increased evaporation dry eye + DWDE Decreased wettability dry eye | 0 | 0 | 0 | **2** | 100% |

FIG.8

METHOD RELATED TO DRY-EYE CLASSIFICATION AND OPHTHALMOLOGIC DEVICE AND LEARNING DEVICE EMPLOYING SAME

CROSS REFERENCE TO RELATED APPLICATIONS

This is a U.S. National Phase Application under 35 U.S.C. § 371 of International Patent Application No. PCT/JP2022/016580, filed Mar. 31, 2022, which claims priority of Japanese Patent Application No. 2021-064437, filed Apr. 5, 2021, each of which is hereby incorporated by reference in its entirety.

FIELD OF THE INVENTION

The present invention is regarding an ophthalmic apparatus and the like which performs measurement regarding the state of a lacrimal fluid layer on a cornea surface of an examination target eye and classifies a dry eye syndrome.

BACKGROUND

Conventionally, a treatment policy is decided by classifying dry eye syndrome by cause. There is a known classification method of a dry eye syndrome which a physician classifies it qualitatively by staining an examination target eye with fluorescein which is a fluorescent substance and observing a disruption patter of a lacrimal fluid layer with a slit lamp (see, for example, Japanese Patent No. 2018-47083A).

Furthermore, an apparatus for improving reliability regarding classification of a breaking pattern of a lacrimal fluid layer has also been proposed (see, for example, Japanese Patent No. 2018-470803A).

Observation of a lacrimal fluid layer with a slit lamp requires staining with fluorescein, which is an invasive test. In addition, it is difficult to unify the method of staining, and the interpretation of the findings may differ depending on the examiner. Therefore, there is a need for a non-invasive and more objective test method.

Although Japanese Patent No. 2018-470803A also describes an apparatus for improving reliability non-invasively, it is necessary to specify a destructive region even in the apparatus, and a threshold value for determining whether or not a destructive region is used for identifying the destructive region. Therefore, there has been a problem that information on a place smaller than a threshold is not used for classification, and there is a possibility that accuracy of classification may be lowered.

The present invention was made in order to solve the above-described problems, and it is an object thereof to provide an ophthalmic apparatus or the like capable of performing classification of a dry eye syndrome with higher accuracy non-invasively and objectively.

SUMMARY

In order to achieve the above-mentioned object, according to one aspect of the present invention, the ophthalmic apparatus which performs measurements regarding the state of a lacrimal fluid layer on a cornea surface of an examination target eye and which classifies a dry eye syndrome using a result of the measurements, comprises a light-projecting unit that projects a predetermined pattern onto a cornea surface, an image capturing unit that repeatedly captures a reflected image of the pattern reflected off the cornea surface, an acquiring unit that acquires blurriness information according to a value indicating a blurriness level at a maximum portion of luminance values in a reflected image, for each of the captured multiple reflected images, a classifying unit that acquires a classification result of a dry eye syndrome by applying multiple pieces of time-series blurriness information acquired by the acquiring unit to a learning model trained using multiple pairs of training input information, which is multiple pieces of time-series blurriness information, and training output information, which is a classification result of a dry eye syndrome corresponding to the training input information, and an output unit that outputs the classification result acquired by the classifying unit.

With this configuration, it is possible to perform measurements non-invasively since the measurements are performed using a reflected image of a predetermined pattern reflected off the cornea surface. Further, it is possible to perform classification more objectively since a dry eye syndrome is classified by applying the measurement result to a learning model. Further, it is possible to perform classification with higher accuracy by applying blurriness information to the learning model. The blurriness information may be an image displaying the multiple values indicating the blurriness level corresponding to multiple measurement points on a cornea surface of the examination target eye, or a numerical sequence in which multiple values indicating the blurriness level corresponding to the multiple measurement points are arranged in a predetermined order.

In addition, the ophthalmic apparatus according to one aspect of the present invention, further comprises a calculating unit that calculates severity information, which is a value according to the sum in a time direction of the values each indicating a blurriness level at a maximum portion of luminance values in the repeatedly captured reflected image, and the output unit may also outputs severity information.

With this configuration, it is possible to know the severity of a dry eye syndrome in the classification result.

In addition, in the ophthalmic apparatus according to one aspect of the present invention, the classification result may be any of an aqueous-deficient type, a decreased wettability type, an increased evaporation type, and a combined type of the increased evaporation type and the decreased wettability type.

Further, a learning model according to one aspect of the present invention is trained using multiple pairs of training input information which is multiple pieces of time-series blurriness information, and training output information which is a classification result of a dry eye syndrome corresponding to the training input information, wherein blurriness information is the one according to a value indicating a blurriness level at a maximum portion of luminance value in a reflected image of the pattern reflected off the cornea surface of an examination target eye, and when multiple pieces of time-series blurriness information of an examination target eye to be classified is applied, a classification result of dry eye syndrome related to an examination target eye to be classified can be acquired.

With this configuration, it is possible to perform classification of a dry eye syndrome non-invasively and objectively by using a learning model. Further, it is possible to perform classification with higher accuracy by applying blurriness information to a learning model.

A method regarding classification of a dry eye syndrome according to one aspect of the present invention is to perform measurement regarding the state of a lacrimal fluid layer on a cornea surface of an examination target eye, and classify a dry eye syndrome using a result of the measurement, comprising a step of projecting a predetermined pattern onto a cornea surface, a step of repeatedly capturing a reflected image of the pattern reflected off the cornea surface, a step of acquiring blurriness information according to a value indicating a blurriness level at a maximum portion of luminance values in a reflected image, for each of the captured multiple reflected images, a step of acquiring a classification result of a dry eye syndrome by applying multiple pieces of time-series blurriness information acquired in the step of acquiring blurriness information, to a learning model trained using multiple pairs of training input information, which is multiple pieces of time-series blurriness information, and training output information, which is a classification result of a dry eye syndrome corresponding to the training input information, and a step of outputting the classification result acquired in the step of acquiring a classification result of a dry eye syndrome.

According to an ophthalmic apparatus or the like according to one aspect of the present invention, it is possible to classify a dry eye syndrome non-invasively and objectively. Further, it is possible to perform classification with higher accuracy by applying blurriness information to a learning model.

BRIEF DESCRIPTION OF DRAWINGS

FIG. 7 is a diagram for explaining an example of each layer of the learner in this embodiment.

FIG. 8 is a diagram showing a correct rate of classification results according to one aspect of the present invention.

DETAILED DESCRIPTION

Figure 1:
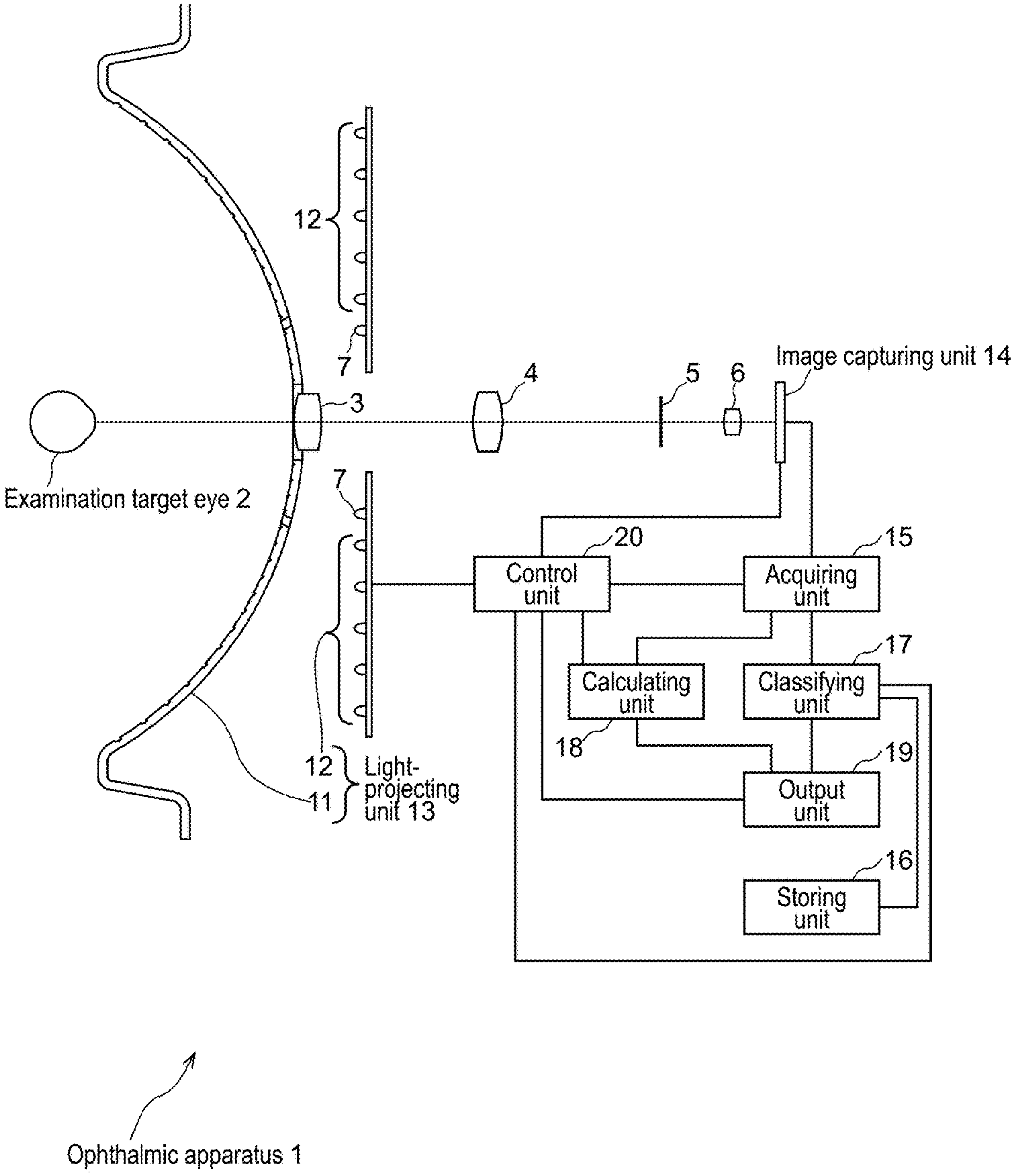
FIG. 1 is a schematic diagram showing a configuration of an ophthalmic apparatus according to an embodiment of the present invention.

Hereinafter, a method for classifying a dry eye syndrome according to the present invention and an ophthalmic apparatus using the method for classifying a dry eye syndrome will be described using an embodiment. It should be noted that constituent elements and steps denoted by the same reference numerals in the following embodiments are the same or corresponding constituent elements and steps, and thus a description thereof may not be repeated. The ophthalmic apparatus according to this embodiment calculates blurriness information of a maximum portion of luminance values of a reflected image of a pattern projected onto a cornea surface, and classifies a dry eye syndrome to a learning model by applying multiple pieces of time-series blurriness information calculated.

FIG. 1 is a schematic diagram showing a configuration of an ophthalmic apparatus 1 according to this embodiment. The ophthalmic apparatus 1 according to this embodiment performs measurement regarding the state of a lacrimal fluid layer on a cornea surface of the examination target eye 2, and classifies a dry eye syndrome using the measurement result, and includes the configuration of an optical system having an ocular lens 3, a field lens 4, a diaphragm (pinhole) 5, and an imaging lens 6, an illumination light source 7, a light-projecting unit 13, an image capturing unit 14, an acquiring unit 15, a storing unit 16, a classifying unit 17, a calculating unit 18, an output unit 19, and a control unit 20. The ophthalmic apparatus 1 may, for example, perform measurement regarding the state of a lacrimal fluid layer to classify a dry eye syndrome, or may have a function such as a keratometer.

The light-projecting unit 13 projects a predetermined pattern onto a cornea surface of the examination target eye 2. The predetermined pattern may be, for example, a linear pattern, a dotted pattern, or may be a combination thereof. The linear pattern may be, for example, a pattern having multiple lines. The line may be, for example, a curved line, or may be a straight line. The pattern having a curved line may be, for example, a pattern having multiple points that are arranged regularly. The dotted pattern may be, for example, a pattern having multiple points. A pattern having multiple points may be, for example, a pattern having multiple points that are arranged regularly, or may be a pattern having multiple points that are arranged randomly. In the case of former, the pattern having multiple points may be a set of multiple points that are arranged at a lattice points on a square lattice, a rectangular lattice, or a triangular lattice, or the like. It is preferable that, in a predetermined pattern, multiple lines have the same width, and multiple points have the same diameter. The pattern is preferably projected over the entire cornea of the examination target eye 2. In this embodiment, a case will be mainly described in which the light-projecting unit 13 has a placido dome 11 and a measurement light source 12, and the predetermined pattern is a pattern having multiple concentric rings, that is, a pattern of multiple rings (a placido ring) formed by the placido dome 11. The placido dome 11 is a dome-shaped optical mask having openings in the shape of multiple concentric rings, through which measurement light emitted from the measurement light source 12 forms a ring pattern, which is a pattern having multiple concentric rings, on the anterior eye part of the examination target eye 2. The wavelength of the measurement light emitted from the measurement light source 12 is not limited. The measurement light may be, for example, visible light or near-infrared light. If the measurement light is visible light, the wavelength may be, for example, 650 nm or 750 nm, or the like. There is no limitation on the method for projecting a ring pattern onto the examination target eye 2. The process of projecting a ring pattern onto the examination target eye 2 is already known, and a detailed description thereof has been omitted.

The illumination light source 7 is a light source for illuminating the examination target eye 2, and illuminates the examination target eye 2 in order to allow an examiner to see the state of an eyelid of an examinee or the like. The illumination light emitted from the illumination light source 7 may be, for example, far infrared light. Each of the illumination light source 7 and the measurement light source 12 may be arranged in a ring-like form about the optical axis of the optical system.

The ring pattern projected onto the cornea surface of the examination target eye 2 is reflected off the cornea surface. The reflected pattern is transmitted through the ocular lens 3, the field lens 4, the diaphragm 5, and the imaging lens 6, and forms an image. The image capturing unit 14 captures a reflected image of the pattern. The image capturing unit 14 may be, for example, a CCD image sensor, a CMOS image sensor, or the like. The image capturing unit 14 may repeatedly capture reflected images of a pattern. The images may be repeatedly captured at predetermined time interval. By capturing the images repeatedly in this way, it is possible to acquire information of the examination target eye 2 in time series.

The acquiring unit 15 calculates blurriness information indicating a blurriness level at a maximum portion of luminance values in the reflected image captured by the image capturing unit 14. If the predetermined pattern has a line, the acquiring unit 15 may calculate blurriness information of a maximum portion of luminance values, in any direction that passes through the point in the captured reflected image. It is preferable that blurriness information regarding a point is blurriness information on a straight line that passes through the center of the point in the reflected image. If a reflected image of a ring pattern is captured, the line in the reflected image is in the shape of a ring. Accordingly, if a reflected image of a ring patter is captured, the acquiring unit 15 specifies a center position in the reflected image of the ring pattern. The center position may be specified, for example, by specifying the center of the ring with the smallest diameter contained in the pattern of multiple rings. The acquiring unit 15 calculates blurriness information at the intersection between the ring pattern and each straight line radially extending at every predetermined angle from the specified center position.

Hereinafter, a method in which the acquiring unit 15 acquires data in the direction of a straight line radially extending from the specified center position will be described. When sampling a luminance value at a point on a straight line radially extending at an angle $\theta$ from the specified center position, the acquiring unit 15 may use luminance values of nearby points at the same distance from the center position. The luminance values of nearby points may be, for example, luminance values on straight lines radially extending from the center position at every $\delta$ from an angle $\theta-n\times\delta$ to the angle $\theta+n\times\delta$. Note that n is an integer of 1 or more, and $\delta$ is a positive real number. In addition, if the acquiring unit 15 acquires data in the direction of a straight line radially extending from the specified center position at angle intervals $\Delta\theta$, it is preferable that $n\times\delta<\Delta\theta/2$. There is not particular limitation on $\Delta\theta$, but it may be, for example, 5 degrees, 10 degrees, 15 degrees, or the like. If $\Delta\theta$ is 10 degrees, luminance values on 36 straight lines radially extending from the center position are sampled. When acquiring a luminance value at the $\theta$ in this manner, the acquiring unit 15 may acquire, as the luminance value at the angle $\theta$, a representative value of 2n+1 luminance values consisting of those at the angles $\theta-n\times\delta$, $\theta-(n-1)\times\delta$, . . . , $\theta$, . . . , $\theta+(n-1)\times\delta$, and $\theta+n\times\delta$. The representative value may be, for example, a mean, a median, a maximum, or the like. Specifically, when acquiring a luminance value on a straight line at an angle $\theta$, the acquiring unit 15 may use a luminance value on a straight line at an angle of $\theta+\delta$, a luminance value on a straight line at an angle of $\theta+2\delta$, a luminance value on a straight line at an angle of $\theta-\delta$, and a luminance value on a straight line at an angle of $\theta-2\delta$. In a similar manner, the acquiring unit 15 may acquire, as luminance values on the straight line corresponding to the angle $\theta$, a representative values of multiple luminance values sequentially from the center side. If the data is acquired in this manner, for example, data of a reflected image even at an angle at which the reflected image of a ring pattern is incomplete can be acquired from data at nearby angles, and the position of the intersection between the radially extending straight line and the ring can be specified. In the description above, a case was described in which the acquiring unit 15 acquires, as a luminance value on a straight line at a given angle $\theta$, a representative value of multiple luminance values including luminance values of nearby points, but there is no limitation to this. For example, the acquiring unit 15 may sample, as data of luminance values on the straight line at an angle of $\theta$, sequentially from the center side. The acquiring unit 15 may acquire, as luminance values on radially extending straight lines, luminance values on straight lines radially extending at every $\Delta\theta$ from the specified center position.

Figure 3A:
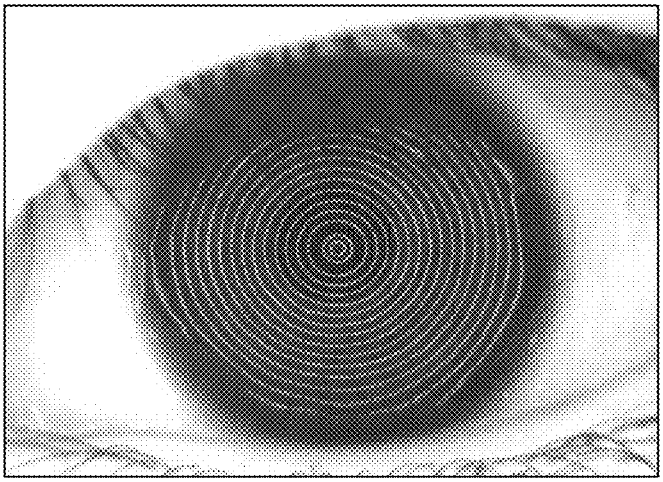
FIGS. 3(*a*), 3(*b*) and 3(*c*) are a diagram illustrating an example of an examination target eye to which a pattern is projected in this embodiment.
Figure 3B:
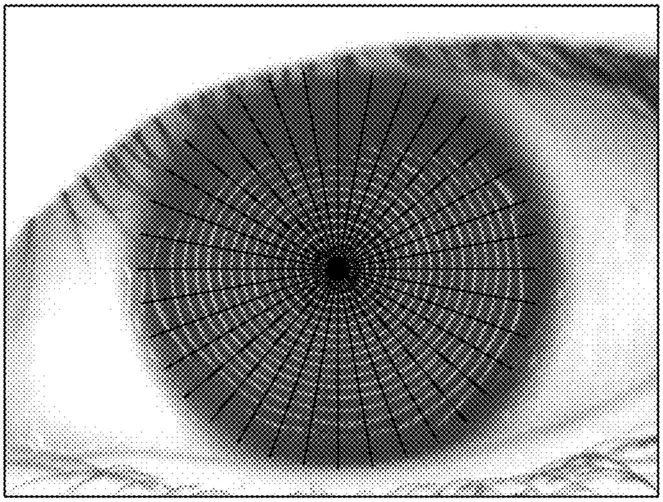
Figure 3C:
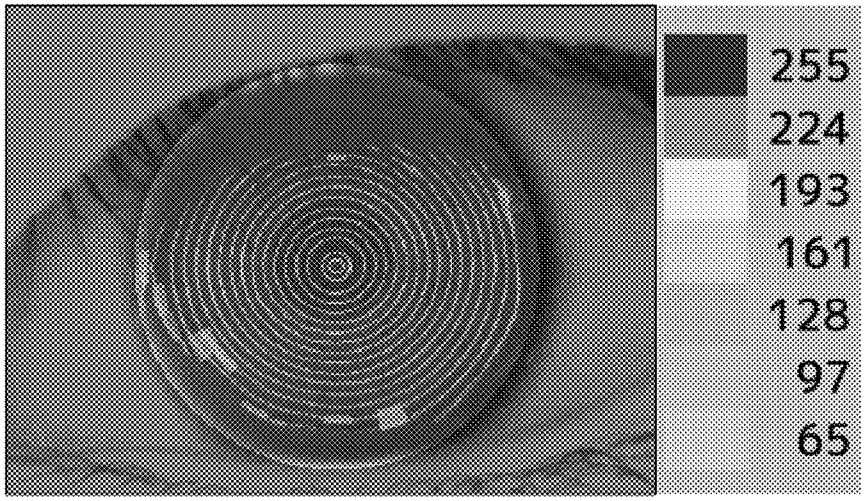
Figure 4A:
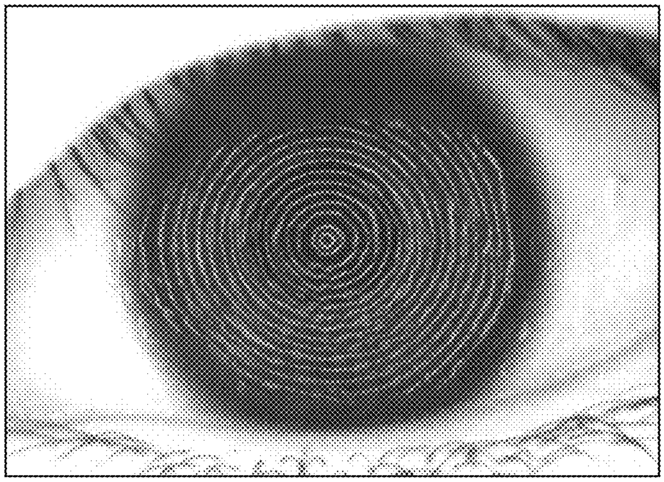
FIGS. 4(*a*), 4(*b*) and 4(*c*) are a diagram illustrating an example of an examination target eye to which a pattern is projected in this embodiment.
Figure 4B:
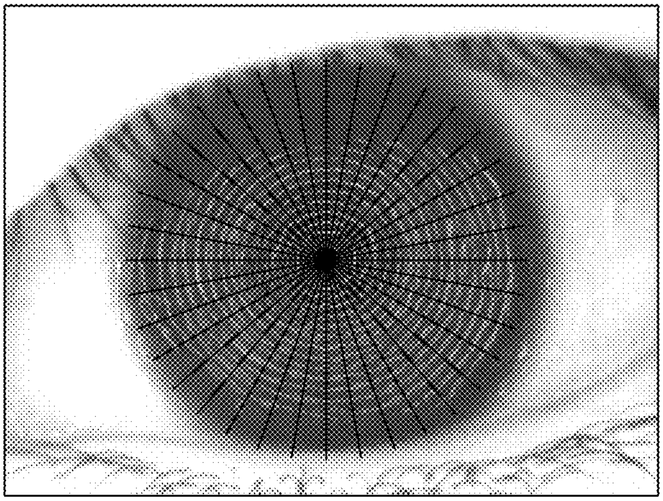
Figure 4C:
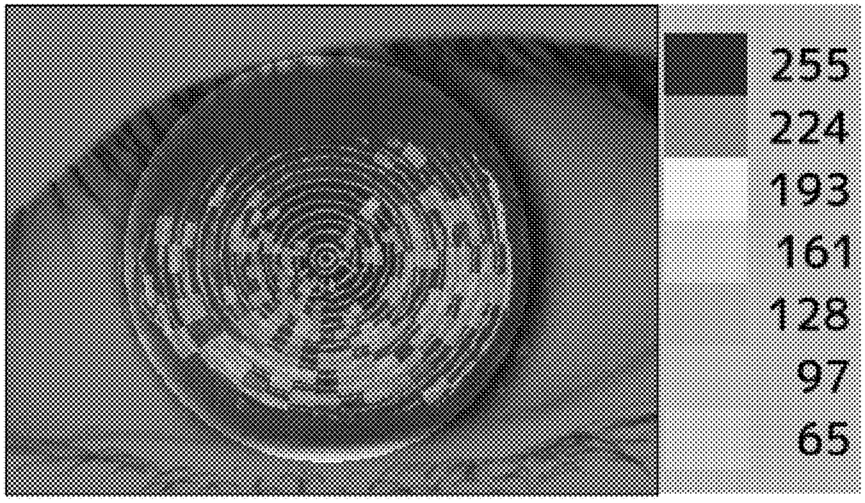

FIG. 3 shows examples of captured images of the examination target eye 2 in which a lacrimal fluid layer on a cornea surface is not broken, and FIG. 4 shows examples of capture image of the examination target eye 2 in which a lacrimal fluid layer on a cornea surface is broken. More specifically, FIG. 3 (*a*) and FIG. 4 (*a*) are captured images of a reflected image of a ring pattern reflected off the cornea surface, FIG. 3 (*b*) and FIG. 4 (*b*) are viewed in which straight lines radially extending a every predetermined angle from the center position are superimposed on the captured image, and FIG. 3 (*c*) and FIG. 4 (*c*) are captured images on which colors each corresponding to the calculated blurriness information are superimposed.

Figure 5:
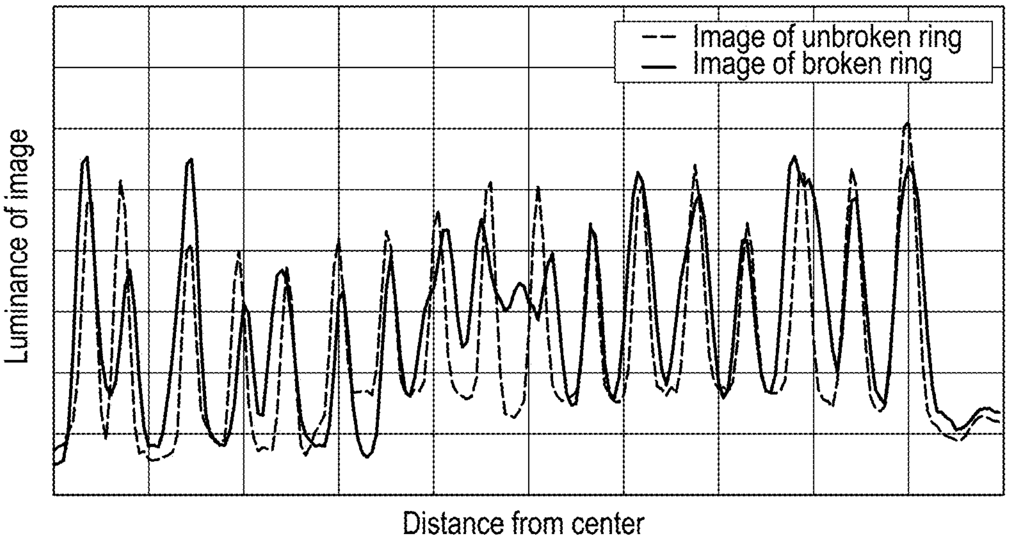
FIG. 5 is a diagram illustrating an example of a change in a luminance value in a radial direction of an examination target eye in this embodiment.

As is clear from a comparison between FIGS. 3(*a*) and 4(*a*), if the lacrimal fluid layer is not broken, the rings of the pattern of multiple rings in the reflected image are not broken, whereas, if the lacrimal fluid layer is broken, the rings of the pattern of multiple rings of the pattern of multiple rings in the reflected image are broken. FIG. 5 shows a relationship between the distance from the center of reflected images of a ring pattern and the luminance values, in a predetermined angular direction. The luminance values shown in FIG. 5 were obtained, for example, through sampling in the above-described manner from a captured image of an examination target eye. In FIG. 5, the change in the luminance values regarding an image in which the rings are not broken, that is, an image of an examination target eye in which the lacrimal fluid layer is not broken is indicated by the broken lines, and the change in the luminance values regarding an image in which the rings are broken, that is, an image of an examination target eye in which the lacrimal fluid layer is broken is indicated by the solid line. In FIG. 5, the luminance values have their peaks at positions of the rings in the reflected images. As is clear from FIG. 5, the shape of the peaks of the luminance values regarding the examination target eye in which the lacrimal fluid layer is broken is blunter than the shape of the peaks of the luminance values regarding the examination target eye in which the lacrimal fluid layer is not broken. In other words, the shape of the peaks of the luminance values regarding the examination target eye in which the lacrimal fluid layer is not broken is sharper than the shape of the peaks of the luminance values regarding the examination target eye in which the lacrimal fluid layer is broken. Accordingly, it is possible to see the level to which the lacrimal fluid layer is broken, by calculating blurriness information indicating the blurriness level of the shape of the peaks of the luminance values, and thus the acquiring unit 15 calculates the blurriness information. The value indicating the blurriness level may be, for example, a measurement result regarding the state of a lacrimal fluid layer on the cornea surface of the examination target eye 2. There is no limitation on the blurriness information calculated by the acquiring unit 15, as long as it is eventually possible to see the blurriness level of a maximum portion (a peak) of luminance values of a reflected image of a pattern. The blurriness information may be, for example, a blurriness level indicated by a value that increases in accordance with an increase in the blurriness level, or may be a sharpness level indicated by a value that decreases in accordance with an increase in the blurriness level. In this embodiment, a case will mainly be described in which the blurriness information is a blurriness level.

The acquiring unit 15 acquires the blurriness information corresponding to a value indicating the blurriness level calculated using a certain captured image. Note that, since the acquiring unit 15 normally calculates multiple values indicating the blurriness level from the captured image, the blurriness information is corresponding to multiple values indicating the blurriness level of the local majority of the luminance value at multiple positions of the reflected image of the pattern. Multiple positions are preferably multiple measurement points in the entire area of the cornea of the examination target eye 2. This is because classification can be performed using information on the entire cornea of the examination target eye 2. The blurriness information may be, for example, information including multiple values indicating the blurriness level, an image displaying multiple values indicating the blurriness level as shown in FIG. 3(*c*) and FIG. 4(*c*), or other information corresponding to multiple values indicating the blurriness level. For example, a value indicating the blurriness level may be displayed in gray scale or color in an image displaying a value indicating the blurriness level. Normally, one piece of blurriness information is acquired from one captured image. Therefore, in response to the reflected image of the pattern being repeatedly captured, the blurriness information is acquired for each of multiple captured reflected images. The multiple pieces of blurriness information obtained in this way are in time series. In this embodiment, a case where the acquiring unit 15 acquires blurriness information, which is an image displaying a value indicating the blurriness degree, will be mainly described.

Figure 6:
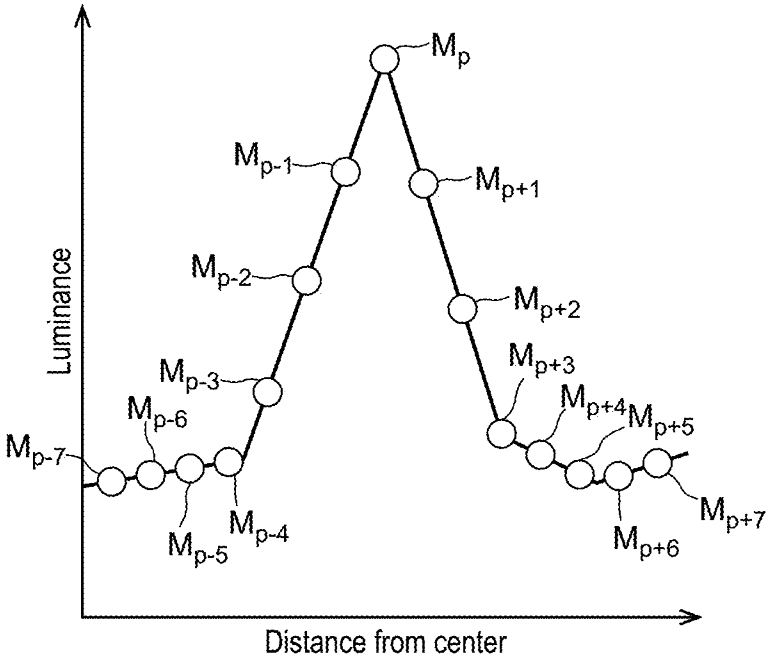
FIG. 6 is an example of luminance in a direction perpendicular to the ring pattern in this embodiment.

Next, a method of calculating the blurriness level by the acquiring unit 15 will be described. FIG. 6 is a diagram showing a relationship between the luminance values regarding one peak and the distance from the center, as acquired in a direction along a straight line at the angle θ. In FIG. 6, each circle mark indicates a relationship between the luminance value at a sampling point and the distance from the center. It is assumed that a sampling point $M_p$ corresponds to a maximum value, wherein the subscript increases or decreases in a direction away from the sampling point $M_p$. The acquiring unit 15 may calculate a blurriness level B regarding a peak using the following formula.

$$B = b - a\sum_{m=-k}^{k} |I_p - I_{p+m}| \qquad \text{Numberical Formula 1}$$

In the formula, a luminance value at a sampling point $M_{p+d}$ is $I_{p+d}$. d is any integer. Accordingly, for example, $I_p$ is a luminance value that is a maximum value. Each of a and b is a constant that is a positive real number, and k is an integer of 1 or more. It is possible to change the influence (sensitivity) of the shape of a peak of luminance values on the blurriness level by changing the value of a. The total in the formula above increases in accordance with an increase in the sharpness of a peak of luminance values, and thus, it is possible to increase the sensitivity by decreasing the value of a. It is preferable that the constant b is determined as appropriate, for example, such that the blurriness level B has a positive value. Furthermore, it is also preferable that k is set to a value at which the shape of a peak of luminance values is properly included, according to the intervals of sampling points of luminance values along the straight line at the angle θ. For example, in the case of FIG. 6, k may be set to 2.

The method for calculating the blurriness level B is merely an example, and it is also possible to calculate a blurriness level using other methods. For example, it is also possible to calculate a blurriness level using a slope of multiple luminance values from a peak to the center side and a slope of multiple luminance values from the peak to the outer side.

The blurriness level B is a value regarding one peak of luminance values, but, as shown in FIG. 5, there are multiple peaks on a straight line at given angle radially extending from the center position of a reflected image of a pattern of multiple rings, and there is such a straight line for every angle Δθ. Accordingly, the acquiring unit 15 may calculate blurriness information for each peak of luminance values, on each straight line radially extending at every predetermined angle from the center position of a reflected image of a pattern of multiple rings. In this manner, it is possible to calculate blurriness information at every measurement point over the entire cornea of an examination target eye 2. The position of each measurement point is the position of the intersection between each straight line radially extending at equal intervals from the center position of the reflected image, and rings of the pattern of multiple rings. The acquiring unit 15 may calculate blurriness information, for example, in a predetermined range or region in the cornea of an examination target eye 2. If reflected images of a pattern are repeatedly captured, the acquiring unit 15 may calculate multiple pieces of blurriness information at measurement points on the cornea, in each reflected image of the repeatedly captured images. The blurriness level is already known, and a detailed description thereof has been omitted. For the acquisition of the blurriness level, see, for example, JP-A-2020-18475. The blurriness level in this embodiment corresponds to the blurriness level in JP-A-2020-18475. The acquiring unit 15 may start the acquisition of blurriness information using the captured image from the time point when the eyelid opening of the examination target eye 2 is detected. For example, the time point at which the reflected image of the pattern is included in the captured image may be the time point at which the eyelid opening is detected.

In a storing unit 16, a learning model is stored. The learning model is learned by using multiple sets of training input information that is multiple pieces of time-series blurriness information and training output information that is a classification result of dry eye corresponding to the training input information. This learning model will be described later. The process in which the learning model is stored in the storing unit 16 is not limited. For example, the learning model may be stored in the storing unit 16 via a storage medium, or the learning model transmitted via a communication line or the like may be stored in the storing unit 16. The storing unit 16 is preferably realized by a non-volatile storage medium, but may be realized by a volatile storage medium. The storage medium may be, for example, a semiconductor memory, a magnetic disk, an optical disk, or the like.

The classifying unit 17 acquires the classification result of a dry eye syndrome by applying multiple pieces of time-series blurriness information calculated by the acquiring unit 15 to the learning model stored in the storing unit 16. The classification result may be, for example, any one selected from the group consisting of an aqueous-deficient dry eye type, a decreased wettability dry eye type, an increased evaporation dry eye type, and a combined type of the decreased wettability dry eye type and the increased evaporation dry eye type. In addition, the classification result may include the fact that it is normal, that is, it is not a dry eye syndrome. In this case, the classification result may be any one selected from, for example, an aqueous-deficient dry eye type, a decreased wettability dry eye type, an increased evaporation dry eye type, a combined type of the decreased wettability dry eye type and the increased evaporation dry eye type, and a normal type. The classification of these dry eye syndromes are known, and detailed description thereof will be omitted. In addition, it is needless to say that the classification of a dry eye syndrome is not limited thereto.

The calculating unit 18 calculates the severity information, which is a value corresponding to the sum of the time directions of the values indicating the blurriness level of the local majority of the luminance value of the repeatedly captured reflected image. The severity information is a value calculated by using the sum of the time directions of the values indicating the blurriness at a maximum portion of the luminance value of the reflected image as described above, and may be, for example, a value that increases as the sum increases. The severity information may be, for example, a sum of values indicating the blurriness level in the time direction, that is, a sum of values indicating the blurriness level in the measurement period, a value indicating the blurriness level per unit time, that is, a value obtained by dividing the sum of the values indicating the blurriness level in the time direction by the measurement time, or a value obtained by dividing the average value of values indicating the blurriness level, that is, the sum of the values indicating the blurriness level in the time direction by the number of blurriness information. The measurement period may be, for example, a period from the start of the acquisition of blurriness information until a predetermined measurement time (for example, 10 seconds) elapses. Here, the value indicating the blurriness level to be the target of the sum is usually a value corresponding to one piece of blurriness information. The value indicating the blurriness level may be, for example, a value calculated by the acquiring unit 15 using a captured image, or may be a value acquired from blurriness information. As the value indicating the blurriness level, for example, a representative value of multiple values (for example, the blurriness level) indicating the blurriness level corresponding to one captured image or one piece of blurriness information may be used. The representative value may be, for example, an average value, a median value, a maximum value, or the like. For example, since the number of values indicating the blurriness level acquired from the captured image may differ from each captured image, it is preferable to use the representative value as described above. As described above, in the case of dry eye syndrome in which breakdown occurs in a lacrimal fluid layer, the blurriness level of the reflected image of the pattern increases. The greater the blurriness level, the more severe the dry eye syndrome will be. Therefore, by calculating the severity information corresponding to the sum of the values indicating the blurriness level in the time direction, a value indicating the severity of dry eye syndrome can be obtained. In addition, the severity information may be any index that indicates the severity as a result. Therefore, the severity information may be, for example, information in which the severity increases as the value increases, or information in which the severity decreases as the value increases. For example, when the object of the summation is the blurriness level, the former is obtained, and when the object of the summation is the kurtosis degree, the latter is obtained.

The output unit 19 performs output regarding the classification result obtained with the classifying unit 17 and the severity information calculated by the calculating unit 18. This output enables the classification result of a dry eye syndrome of an examination target eye 2 and the severity thereof to be known. The output may be, for example, display on a display device (e.g., a liquid crystal display, an organic EL display, etc.), transmission via a communication line to a predetermined device, printing by a printer, sound output by a speaker accumulation in a storage medium, or delivery to another constituent element. The output unit 19 may or may not include a device that performs output (e.g., a display device, a printer, etc.). The output unit 19 may be realized by hardware, or may be realized by software such as a driver that drives these devices.

The control unit 20 performs control of processing timings and the like regarding on/off of the measurement light source 12, image capturing by the image capturing unit 14, acquisition of blurriness information by the acquiring unit 15, classification of dry eye syndrome by the classifying unit 17, calculation of severity information by the calculating unit 18, and output by the output unit 19, and the like.

Next, a learning model used for classifying dry eye syndrome will be described. As described above, a learning model is learned by using multiple sets of training input information and training output information. The set of training input information and training output information may be referred to as training information. The learning model may be, for example, a learning result of a neural network (NN: Neural Network) or a learning result of another machine learning. The neural network may be, for example, a convolutional neural network (CNN: Convolutional Neural Network) or another neural network (e.g., a neural network composed of all coupled layers). A convolutional neural network is a neural network having one or more convolutional layers. Further, when the neural network has at least one intermediate layer (hidden layer), learning of the neural network may be considered as deep learning (deep learning, Deep Learning). In the case where a neural network is used for machine learning, the number of layers of the neural network, the number of nodes in each layer, the type of each layer (e.g., a convolutional layer, a total combined layer, and the like) and the like may be appropriately selected. The number of nodes of the input layer and the output layer is usually determined by the training input information and the training output information included in the training information. In this embodiment, the information input to the learning model is multiple pieces of time-series blurriness information. As described above, the blurriness information may be, for example, a two-dimensional image or a numerical sequence in which multiple values indicating the blurriness degree are arranged in a predetermined order. The input to the learning model results in such blurriness information being aligned along the time series. When blurriness information is a two-dimensional image, the input to the learning model is three-dimensional information in which the spatial direction is two-dimensional and the temporal direction is one-dimensional. When blurriness information is a numerical sequence, the input to the learning model is information in which such numerical sequences are arranged in time series. In this embodiment, a case where the input to the learning model is three-dimensional information in which two-dimensional images are arranged in time series will be mainly described.

Note that the learning model is stored in the storing unit 16 may be, for example, that the learning model itself (e.g., a function for outputting a value to an input, a model of a learning result, or the like) is stored, or that information such as parameters necessary for configuring the learning model is stored. This is because even in the latter case, since the learning model can be configured using information such as the parameter, it can be considered that the learning model is substantially stored in the storing unit 16. In this embodiment, a case where the learning model itself is stored in the storing unit 16 will be mainly described.

Here, the generation of the learning model will be described. The learning model is generated by learning multiple pieces of training information as described above. The training input information may be, for example, a measurement result related to the examination target eye, that is, multiple pieces of time-series blurriness information acquired by the acquiring unit 15. Further, the training output information may be, for example, a classification result of a dry eye syndrome classified by an expert such as a doctor with respect to the examination target eye, the training input information being a set with the training output information. The training output information is the same as the classification result by the classifying unit 17. Therefore, the training output information may be, for example, any one selected from the group consisting of an aqueous-deficient dry eye type, a decreased wettability dry eye type, an increased evaporation dry eye type, and a combined type of the decreased wettability dry eye type and the increased evaporation dry eye type, and may be any one selected from the group consisting of an aqueous-deficient dry eye type, a decreased wettability dry eye type, an increased evaporation dry eye type, a combined type of the decreased wettability dry eye type and the increased evaporation dry eye type, and normal. In addition, in a case where another classification is performed by the classifying unit 17, the training output information may be in accordance with the classification.

A learning model is generated by learning multiple sets of training input information and training output information. The learning model is a result of multiple sets of machine learning of training input information that is multiple time-series blurriness information and training output information that is a classification result of a dry eye syndrome corresponding to the training input information. Therefore, when multiple time-series blurriness information the examination target eye 2 to be classified is applied to the learning model, the classification result of a dry eye syndrome for the examination target eye 2 to be classified can be acquired. It is preferable that the training input information and multiple time-series blurriness information of the examination target eye 2 to be classified are the same information. That is, it is preferable that the time interval of the blurriness information of both pieces of information, the number of pieces of blurriness information, the number of pixels of one piece of blurriness information, the number of pieces of information, and the like are the same.

The neural network of the learning model may be, for example, a neural network for classifying multiple time-series images (i.e., three-dimensional information), or may be a neural network for classifying multiple time-series numerical sequences. For example, a 3D-CNN is known as a neural network used to classify three-dimensional data including time-direction. As in the latter case, for example, a neural network having all the coupling layers may be used as a neural network for classifying multiple time-series numerical sequences. In this embodiment, the learning model is the learning result of 3D-CNN.

Although the configuration of each layer of 3D-CNN is not particularly limited, for example, the configuration shown in FIG. 7 may be used. The input size and the output size indicate the number of information in the time direction, the number of pixels in the X-axis direction, the number of pixels in the Y-axis direction, and the number of channels, respectively. That is, the information in which 100 pieces of blurriness information, which is an image of 150×150, are arranged in the time direction, is input to the learning model. The blurriness information may be, for example, an image showing the blurriness degree in a gray scale of 8 bits (256 steps), as in FIG. 3C and FIG. 4C. By acquiring an image of such blurriness information every 0.1 seconds for 10 seconds, 100 pieces of time-series blurriness information may be acquired, which may be an input to the learning model. The size and stride are (the number of information in the time direction, the number of pixels in the X-axis direction, and the number of pixels in the Y-axis direction). Since the number of information in the time direction of the size and the stride is "1", convolution and pooling are performed only in the direction of the two-dimensional image, that is, in the spatial direction. The neural network shown in FIG. 7 has three consecutive sets of convolutional layers and pooling layers. In these layers, no processing is performed in the temporal direction, so that the processing is the same as CNN for normal images. The neural network of FIG. 7 has a pooling layer 4 and an output layer for performing global max pooling after those layers. In this pooling layer 4, processing is also performed in the time direction, and information for 64 channels is output. In addition, in the output layer, after the processing in all the coupling layers is performed, normalization is performed by the soft max function. Thus, the sum of the final four outputs is 1. Then, the classification of a dry eye syndrome corresponding to the output of the maximum value out of the four outputs is acquired as the classification result of the examination target eye 2. For example, the four outputs may correspond to an aqueous-deficient dry eye type, a decreased wettability dry eye type, an increased evaporation dry eye type, and a combined type of the decreased wettability dry eye type and the increased evaporation dry eye type, respectively. Then, for example, in a case where the classification corresponding to the output of the maximum value is an aqueous-deficient dry eye type, the classifying unit 17 acquires an "aqueous-deficient dry eye type" as the classification result of the dry eye syndrome corresponding to the examination target eye 2.

Note that each layer of the neural network shown in FIG. 7 performs padding as appropriate. This padding may be, for example, zero padding, padding to extrapolate the pixel value at the outermost periphery of the image, or padding to be the pixel value folded back at each side of the image. Although an example in which padding is performed is shown in FIG. 7, padding may not be performed.

In addition, it is needless to say that the filter, the pooling size, and the stride value are not limited to those shown in FIG. 7. In the neural network of FIG. 7, processing in the spatial direction is performed first, and then processing in the temporal direction is performed. A (2+1) D-CNN is known as a CNN for performing processes in such an order. Therefore, the learning model according to this embodiment may be a (2+1) D-CNN learning outcome. In the neural network of FIG. 7, each convolution is performed for the spatial direction, while pooling is performed for the temporal direction, the convolution may also be performed for the temporal direction. Further, as the learning model of this embodiment, for example, a learning result of another 3D-CNN may be used, or a learning result of a neural network other than these may be used. In addition, the neural network shown in FIG. 7 may have a batch regularization layer or an activation layer at a stage subsequent to the pooling layer, for example. As described above, as the neural network of the learning model, various types can be used as long as multiple pieces of time-series blurriness information can be classified.

In addition, a bias may or may not be used in each layer of the neural network of the learning model. Whether to use a bias may be determined independently for each layer. The bias may be, for example, a layer-by-layer bias or a filter-by-filter bias. In the former case, one bias is used in each layer, and in the latter case, one or more biases (equal to the number of filters) are used in each layer. When a bias is used in the convolution layer, a result obtained by multiplying each pixel value by a parameter of a filter and adding the bias to the result is input to the activation function.

Each setting in the neural network may be as follows. The activation function may be, for example, a ReLU (normalized linear function), a sigmoid function, or another activation function. Further, in the learning model, for example, an error back propagation method may be used, and a mini batch method may be used. The loss function (error function) may be a mean square error. In addition, although epoch count (the number of times the parameter is updated) is not particularly limited, it is preferable that epoch count that does not cause excessive adaptation is selected. Also, dropouts may be made between predetermined layers to prevent over-fitting. As a learning method in machine learning, a known method can be used, and a detailed description thereof will be omitted.

With the ophthalmic apparatus 1 in this embodiment, an experiment of classifying a dry eye syndrome of the examination target eye 2 using a learning model was performed. In this experiment, using the neural network similar to the neural network of FIG. 7, a dry eyes syndrome were classified into four types: an aqueous-deficient dry eye type, a decreased wettability dry eye type, an increased evaporation dry eye type, a combined type of the decreased wettability dry eye type and the increased evaporation dry eye type. The number of training information (training data) used for machine learning of the learning model used in this experiment is as follows. As the training output information included in the training information, the classification result of the expert was used.

Aqueous-deficient dry eye type: 522
Decreased wettability dry eye type: 630
Increased evaporation dry eye type: 270
A combined type of the decreased wettability dry eye type and the increased evaporation dry eye type: 54

Using the learning model that has performed machine learning as described above, multiple pieces of blurriness information along 56 sets of time series that are not used for machine learning are classified. For the examination target eye corresponding to the 56 sets of information, a dry eye syndrome was classified by an expert, and the correctness of the classification result using the learning model of this experiment was evaluated. FIG. 8 is a diagram showing classification results and correctness and error in the present experiment. For example, as shown in FIG. 8, among the eyes that were judged to be of an aqueous-deficient dry eye type by the expert, 18 eyes were correctly classified, and one eye was misclassified. In FIG. 8, a portion where the correct classification is performed is shaded. In this experiment, 47 of the 56 categories were correctly classified, and therefore, the overall correct answer rate was found to be about 84%. It is considered that the correct answer rate can be further improved by, for example, increasing the number of training information.

Next, an operation of the ophthalmic apparatus 1 will be described with reference to the flowchart in FIG. 2. The illumination light source 7 may be on during the measurement period regarding blurriness information. In this flowchart, it is assumed that the acquiring unit 15 acquires one piece of blurriness information from one captured image.

(Step S101) Alignment that aligns the examination target eye 2 and the optical system of the ophthalmic apparatus 1 in a proper positional relation is performed. This alignment process may be mutually performed, or automatically performed.

(Step S102) The control unit 20 judges whether or not the alignment has been completed. If the alignment has been completed, the procedure advances to step S103, and, if not, the procedure returns to step S101. The judgement may be performed, for example, using a captured image acquired by the image capturing unit 14.

(Step S103) The control unit 20 turns on the measurement light source 12. As a result, a ring pattern is projected onto the cornea surface of the examination target eye 2. The control unit 20 controls the image capturing unit 14 such that reflected images of a ring pattern are captured at predetermined time intervals over a predetermined period (e.g., 10 seconds, 15 seconds, or the like). As a result, the image capturing unit 14 repeatedly acquires the captured images of the reflected image. The number of times that an image is captured in one second may be, for example, five times, ten times, or the like. The acquired multiple captured images may be stored in an unshown storage medium.

(Step S104) The control unit 20 instructs the acquiring unit 15 to perform calculation of a blurriness level of each of the multiple captured images. According to the instruction, the acquiring unit 15 perform calculation of the multiple blurriness levels for each captured image. In the calculation of the blurriness degree, for example, the acquiring unit 15 may or may not specify the center position of the reflected image of the ring pattern for each captured image. In the case of latter, it is also possible that the center position specified in a first captured image is used as the center position in other captured images. The acquiring unit 15 acquires blurriness information corresponding to multiple blurriness degrees for each captured image. In this way, multiple time-series blurriness information is acquired. Note that, for example, the acquiring unit 15 may start the calculation of the blurriness degree and the acquisition of blurriness information from the point in time when the eyelid opening of the examination target eye 2 is detected in the captured image.

(Step S105) The control unit 20 instructs the classifying unit 17 to perform classification of a dry eye syndrome. According to the instruction, the classifying unit 17 perform acquisition of the classification result by applying multiple pieces of time-series blurriness information to the learning model in the storing unit 16. Applying multiple pieces of blurriness information to the learning model may be inputting multiple piece of blurriness information to the learning model. The acquisition of the classification result may be performed using an output from the learning model.

(Step S106) The control unit 20 instructs the calculating unit 18 to perform calculation the severity information. According to the instruction, the calculating unit 18 perform calculation of the severity information corresponding to the sum of the time directions of the values indicating the blurriness degree.

(Step S107) The control unit 20 instructs the output unit 19 to perform output of the classification result and the severity information. According to the instruction, the output unit 19 performs output of the classification result of a dry eye syndrome acquired by the classifying unit 17 and the severity information calculated by the calculating unit 18. Then, a series of processes such as the acquisition of classification and severity information regarding a dry eye syndrome of the examination target eye 2, and the output thereof ends.

Figure 2:
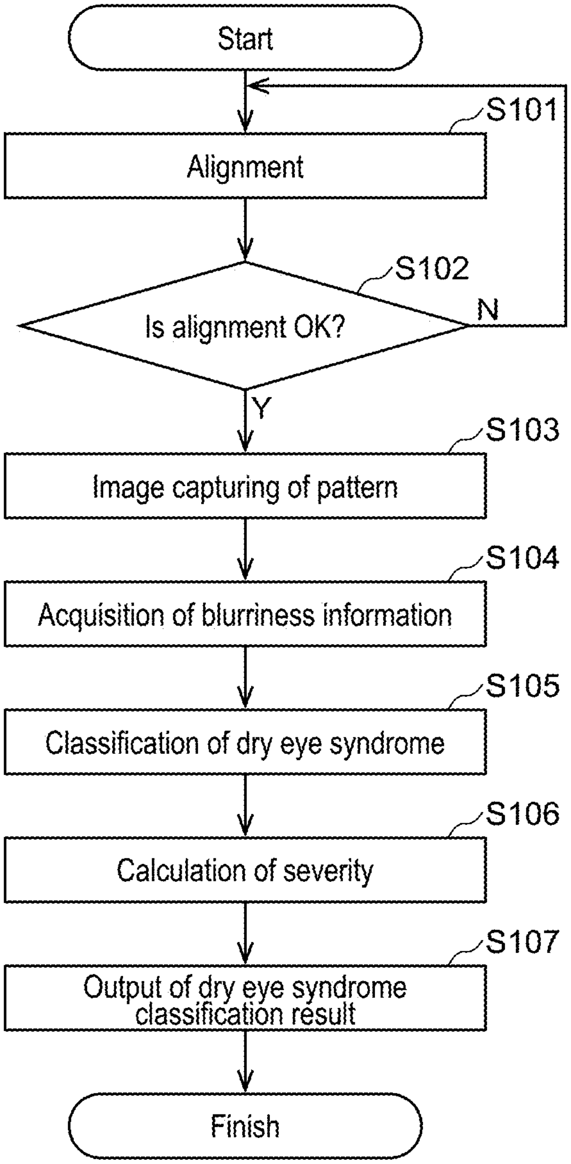
FIG. 2 is an operation flowchart of an ophthalmic apparatus in this embodiment.

The processing order of in the flowchart of FIG. 2 is merely an example, and the order of the steps may be changed as long as similar effects can be obtained.

As described above, according to the method related to classification of a dry eye syndrome according to the present method and ophthalmic apparatus 1 using the method, it is possible to perform measurement related to the state of a lacrimal fluid layer on the cornea surface of the examination target eye 2 and classify a dry eye syndrome of the examination target eye 2 using the results of that measurement. In this embodiment, since the measurement is performed using a reflected image of a predetermined pattern reflected on the cornea surface of the examination target eye 2, the examination target eye 2 does not need to be stained, and non-invasive measurement can be realized. Further, in the classification, by applying multiple time-series blurriness information to the learning model, an objective classification can also be realized. Further, by applying blurriness information to the learning model, it is possible to perform the classification using the information of the region other than the destructive region, it is possible to realize a classification with higher accuracy. Further, by calculating the severity information, the severity of a dry eye syndrome in each classification result can also be known.

In this embodiment, the case in which the severity information is calculated has been described, but this is not necessarily the case. When the severity information is not calculated, the ophthalmic apparatus 1 may not include the calculating unit 18, and the output unit 19 may not output the severity information.

Further, in this embodiment, a case in which the classification using the learning model is performed by the ophthalmic apparatus 1 has been mainly described, but this may not be the case. The classification processing may be performed in an apparatus other than the ophthalmic apparatus using multiple pieces of time-series blurriness information acquired in the ophthalmic apparatus. In this case, in another apparatus, the classification result of a dry eye syndrome of the examination target eye may be acquired by applying multiple pieces of time-series blurriness information of the examination target eye to be classified to the learning model.

In addition, in this embodiment, a case has been described in which blurriness information is acquired by performing measurement on the state of a lacrimal fluid layer on the cornea surface of the examination target eye, or severity information is acquired, but the ophthalmic apparatus 1 according to this embodiment may be used to acquire blurriness information on a lacrimal fluid layer on the surface of a contact lens, such as a soft contact lens, attached to the examination target eye, or to calculate a value (e.g., information similar to severity information) corresponding to the sum of the time directions of the values indicating the blurriness degree at a maximum portion of the luminance value of the reflected image repeatedly captured. Then, by using blurriness information or the like acquired for the contact lens, it may be checked whether or not the contact lens attached to the examination target eye is appropriate.

Furthermore, in the foregoing embodiment, each process or each function may be realized through centralized processing using a single apparatus or a single system, or may be realized through distributed processing using multiple apparatuses or multiple systems.

Furthermore, in the foregoing embodiment, information transmission performed between constituent elements may be such that, for example, if two constituent elements for transmitting information are physically different from each other, the transmission is performed by one of the constituent elements outputting the information and the other constituent element accepting the information, or alternatively, if two constituent elements for transmitting information are physically the same, the transmission is performed by shifting from a processing phase corresponding to one of the constituent elements to a processing phase corresponding to the other constituent element.

Furthermore, in the foregoing embodiment, information relating to the processing performed by each constituent element, for example, information that is to be accepted, acquired, selected, generated, transmitted, or received by each constituent element, information such as a threshold value, a numerical expression, or an address used by each constituent element in the processing and the like may be retained in an unshown storage medium temporarily or for a long period of time even if not specified in the description above. Furthermore, information may be accumulated in the unshown storage medium by each constituent element or by an unshown accumulating portion, Furthermore, information may be read from the unshown storage medium by each constituent element or by an unshown reading portion.

Furthermore, in the foregoing embodiment, if information used in each constituent element or the like, for example, information such as a threshold value, an address, or various setting values used by each constituent element in the processing may be changed by a user, the user may or may not be allowed to change such information as appropriate even through this is not specified in the description above. If the user is allowed to change such information, the change may be realized by, for example, an unshown accepting portion that accepts a change instruction made by the user and an unshown changing portion that changes information according to the change instruction. The change instruction may be accepted by the unshown accepting portion, for example, by accepting information from an input device, by receiving information transmitted via a communication line, or aby accepting information read from a predetermined storage medium.

Furthermore, in the foregoing embodiment, each constituent element may be configured by dedicated hardware, or alternatively, constituent elements that can be realized by software may be realized by executing a program. For example, each constituent element may be realized by a program execution unit such as a CPU reading and executing a software program stored in a storage medium such as a hard disk or a semiconductor memory. When executing the program, the program execution unit may execute the program while accessing the storage unit or the storage medium. Furthermore, this program may be executed as a result of being downloaded from a server or the like, or may be executed by reading a program stored in a predetermined storage medium (e.g., an optical disk such as a CD-ROM, a magnetic dis, a semiconductor memory, etc.). Furthermore, the program may be used as a program forming a program product. That is to say, centralized processing may be performed, or distributed processing may be performed.

The present invention is not limited to the embodiment set forth herein. Various modifications are possible within the scope of the invention.

As described above, the ophthalmic apparatus according to one aspect of the present invention, it is possible to obtain an effect that a dry eye syndrome can be classified non-invasively and objectively, and it is useful as an ophthalmic apparatus and the like for classifying a dry eye syndrome.

The invention claimed is:

1. An ophthalmic apparatus for performing measurement regarding the state of a lacrimal fluid layer on a cornea surface of an examination target eye, and classifying a dry eye syndrome using a result of the measurement, comprising:

a light-projecting unit that projects a predetermined pattern onto a cornea surface;

an image capturing unit that repeatedly captures a reflected image of the pattern reflected off the cornea surface;

an acquiring unit that acquires blurriness information according to a value indicating a blurriness level at a maximum portion of luminance values in a reflected image, for each of the captured multiple reflected images;

a classifying unit that acquires a classification result of a dry eye syndrome by applying multiple pieces of time-series blurriness information acquired by the acquiring unit to a learning model trained using multiple pairs of training input information, which is multiple pieces of time-series blurriness information, and training output information, which is a classification result of a dry eye syndrome corresponding to the training input information; and an output unit that outputs the classification result acquired by the classifying unit.

2. The ophthalmic apparatus according to claim 1, further comprising a calculating unit that calculates severity information, which is a value according to the sum in a time direction of the values each indicating a blurriness level at a maximum portion of luminance values in the repeatedly captured reflected image, wherein the output unit also outputs the severity information.

3. The ophthalmic apparatus according to claim 1, wherein the classification result is any of an aqueous-deficient type, a decreased wettability type, an increased evaporation type, and a combined type of the increased evaporation type and the decreased wettability type.

4. A method regarding classification of a dry eye syndrome, for performing measurement regarding the state of a lacrimal fluid layer on a cornea surface of an examination target eye, and classifying a dry eye syndrome using a result of the measurement, comprising:

a step of projecting a predetermined pattern onto a cornea surface;

a step of repeatedly capturing a reflected image of the pattern reflected off the cornea surface;

a step of acquiring blurriness information according to a value indicating a blurriness level at a maximum portion of luminance values in a reflected image, for each of the captured multiple reflected images;

a step of acquiring a classification result of a dry eye syndrome by applying multiple pieces of time-series blurriness information acquired in the step of acquiring blurriness information, to a learning model trained using multiple pairs of training input information, which is multiple pieces of time-series blurriness information, and training output information, which is a classification result of a dry eye syndrome corresponding to the training input information; and a step of outputting the classification result acquired in the step of acquiring a classification result of a dry eye syndrome.

* * * * *